(12) United States Patent
Traxer

(10) Patent No.: US 11,871,911 B2
(45) Date of Patent: Jan. 16, 2024

(54) MONITORING SYSTEM

(71) Applicant: FERTON HOLDING S.A., Delémont (CH)

(72) Inventor: Olivier Traxer, Paris (FR)

(73) Assignee: FERTON HOLDING S.A., Delémont (CH)

( * ) Notice: Subject to any disclaimer, the term of this patent is extended or adjusted under 35 U.S.C. 154(b) by 348 days.

(21) Appl. No.: 15/525,213

(22) PCT Filed: Nov. 4, 2015

(86) PCT No.: PCT/EP2015/075671
§ 371 (c)(1),
(2) Date: May 8, 2017

(87) PCT Pub. No.: WO2016/071383
PCT Pub. Date: May 12, 2016

(65) Prior Publication Data
US 2017/0325673 A1 Nov. 16, 2017

(30) Foreign Application Priority Data
Nov. 6, 2014 (DE) .................... 10 2014 116 221.8

(51) Int. Cl.
*A61B 5/00* (2006.01)
*A61B 1/307* (2006.01)
(Continued)

(52) U.S. Cl.
CPC ............ *A61B 1/307* (2013.01); *A61B 5/6851* (2013.01); *A61B 5/0215* (2013.01); *A61B 5/036* (2013.01);
(Continued)

(58) Field of Classification Search
CPC ....... A61B 1/307; A61B 1/313; A61B 1/3132; A61B 5/6851; A61B 5/6847;
(Continued)

(56) References Cited

U.S. PATENT DOCUMENTS 6,394,977 B1 * 5/2002 Taylor .................. A61M 25/10
604/100.01
7,025,734 B1 * 4/2006 Ellis .................. A61B 5/14542
600/345
(Continued)

FOREIGN PATENT DOCUMENTS

DE 3880849 T2 12/1993
EP 1539031 B1 1/2013
(Continued)

OTHER PUBLICATIONS

International Search Report for corresponding application PCT/EP2015/075671 filed Nov. 4, 2015; dated Feb. 2, 2016.
(Continued)

*Primary Examiner* — May A Abouelela
(74) *Attorney, Agent, or Firm* — CANTOR COLBURN LLP

(57) ABSTRACT

The invention relates to a monitoring system for endoscopic treatments, in particular for endourological interventions, comprising an evaluation unit (10) and a guide wire (20) which has at least one measurement device (40). According to the invention, the evaluation unit (10) can receive data of the at least one measurement device (40), and the evaluation unit (10) comprises a comparator that compares the data with a comparison value.

9 Claims, 1 Drawing Sheet

(51) Int. Cl.
  *A61B 17/22*   (2006.01)
  *A61B 90/00*   (2016.01)
  *A61B 5/03*    (2006.01)
  *A61B 5/0215*  (2006.01)
  *A61B 17/34*   (2006.01)

(52) U.S. Cl.
  CPC . *A61B 17/3415* (2013.01); *A61B 2017/22042* (2013.01); *A61B 2017/22084* (2013.01); *A61B 2090/064* (2016.02)

(58) Field of Classification Search
  CPC ... A61B 5/6843; A61B 5/6846; A61B 5/0215; A61B 5/02156; A61B 5/02158; A61B 5/02141; A61B 5/03; A61B 5/036; A61B 17/3415; A61B 2017/22042; A61B 2017/22044; A61B 2017/22045; A61B 2017/22038; A61B 2017/22084; A61B 2090/064; A61B 2090/065
  See application file for complete search history.

(56) References Cited

U.S. PATENT DOCUMENTS

| | | | | |
|---|---|---|---|---|
| 7,751,882 B1* | 7/2010 | Helland | | A61B 5/318 607/9 |
| 9,215,964 B2* | 12/2015 | Loske | | A61B 1/00135 |
| 9,282,985 B2* | 3/2016 | Finkman | | A61B 1/07 |
| 9,301,871 B2* | 4/2016 | Kulstad | | A61F 7/12 |
| 10,413,211 B2* | 9/2019 | Kassab | | A61B 5/0538 |
| 2004/0087831 A1* | 5/2004 | Michels | | A61B 17/3415 600/114 |
| 2006/0129091 A1* | 6/2006 | Bonnette | | A61B 17/22 604/93.01 |
| 2008/0082045 A1* | 4/2008 | Goldfarb | | A61B 1/0684 604/96.01 |
| 2009/0192413 A1* | 7/2009 | Sela | | A61M 25/09 600/585 |
| 2009/0260625 A1* | 10/2009 | Wondka | | A61M 16/0459 128/205.25 |
| 2010/0094143 A1* | 4/2010 | Mahapatra | | A61B 17/3401 604/246 |
| 2010/0198191 A1 | 8/2010 | Clifford | | |
| 2010/0234698 A1* | 9/2010 | Manstrom | | A61M 25/09 600/478 |
| 2010/0241008 A1* | 9/2010 | Belleville | | A61B 5/0215 600/478 |
| 2011/0152721 A1* | 6/2011 | Sela | | A61B 5/01 600/585 |
| 2011/0202039 A1* | 8/2011 | Schaaf | | A61B 1/018 604/540 |
| 2011/0208185 A1* | 8/2011 | Diamant | | A61B 18/1492 606/42 |
| 2011/0224666 A1* | 9/2011 | Davies | | A61B 18/1492 606/41 |
| 2012/0172888 A1* | 7/2012 | Shugrue | | A61B 17/42 606/119 |
| 2012/0283582 A1* | 11/2012 | Mahapatra | | A61B 5/7257 600/485 |
| 2013/0079702 A1* | 3/2013 | Klein | | A61M 3/0208 604/22 |
| 2013/0237864 A1 | 9/2013 | Mazar | | |
| 2013/0253498 A1* | 9/2013 | Germain | | A61B 90/08 606/28 |
| 2013/0289369 A1* | 10/2013 | Margolis | | A61B 5/01 606/41 |
| 2013/0317372 A1* | 11/2013 | Eberle | | A61B 5/6851 600/478 |
| 2013/0345670 A1* | 12/2013 | Rajagopalan | | A61M 5/178 606/1 |
| 2014/0005536 A1* | 1/2014 | Burkett | | A61B 5/02158 600/488 |
| 2014/0005558 A1* | 1/2014 | Gregorich | | A61B 5/6851 600/480 |
| 2014/0081244 A1* | 3/2014 | Voeller | | A61B 5/6851 604/528 |
| 2014/0142398 A1* | 5/2014 | Patil | | A61B 5/0538 600/301 |
| 2014/0187972 A1* | 7/2014 | Burkett | | A61B 5/6851 600/481 |
| 2014/0200428 A1* | 7/2014 | Kassab | | A61B 5/0538 600/547 |
| 2014/0200568 A1* | 7/2014 | Sharma | | A61B 18/04 606/27 |
| 2014/0228841 A1* | 8/2014 | Davies | | A61B 18/1492 606/45 |
| 2014/0236118 A1* | 8/2014 | Unser | | A61B 8/06 604/503 |
| 2014/0275950 A1 | 9/2014 | Hoseit | | |
| 2014/0276027 A1* | 9/2014 | Gaddis | | A61B 5/4848 600/459 |
| 2014/0276036 A1 | 9/2014 | Collins | | |
| 2014/0276110 A1 | 9/2014 | Hoseit | | |
| 2014/0276117 A1* | 9/2014 | Burkett | | A61B 5/6851 600/479 |
| 2014/0276138 A1* | 9/2014 | Millett | | A61B 5/6851 600/585 |
| 2014/0287048 A1 | 9/2014 | Reynolds | | |
| 2014/0330262 A1* | 11/2014 | Jannicke | | A61B 18/02 606/21 |
| 2014/0357946 A1* | 12/2014 | Golden | | A61B 17/0218 600/104 |
| 2014/0366874 A1* | 12/2014 | Deutsch | | A61B 5/7278 128/202.13 |
| 2015/0051499 A1* | 2/2015 | McGowan | | A61B 5/0084 600/478 |
| 2015/0223707 A1* | 8/2015 | Ludoph | | A61B 5/6852 600/487 |
| 2015/0305633 A1* | 10/2015 | McCaffrey | | A61B 5/02158 600/486 |
| 2015/0313634 A1* | 11/2015 | Gross | | A61B 1/0676 606/185 |
| 2016/0000341 A1* | 1/2016 | Rotman | | A61B 5/0215 600/486 |
| 2016/0029960 A1* | 2/2016 | Toth | | A61B 5/11 606/41 |
| 2016/0120415 A1* | 5/2016 | Webler | | A61B 5/02158 600/486 |
| 2016/0128781 A1* | 5/2016 | Blohm | | A61B 34/30 606/130 |
| 2016/0213313 A1* | 7/2016 | Toth | | A61B 5/4848 |
| 2016/0310020 A1* | 10/2016 | Warnking | | A61B 5/6852 |

FOREIGN PATENT DOCUMENTS

| | | |
|---|---|---|
| JP | 10276980 A | 10/1998 |
| JP | 2002507733 A | 3/2002 |
| JP | 2003534056 A | 11/2003 |
| JP | 2004532706 A | 10/2004 |
| JP | 2007244679 A | 9/2007 |
| JP | 2010057541 A | 3/2010 |
| JP | 2014507986 A | 4/2014 |
| WO | 9607351 A1 | 3/1996 |
| WO | 2014025255 A1 | 2/2014 |
| WO | 2014106186 A1 | 7/2014 |
| WO | 2014145469 A1 | 9/2014 |

OTHER PUBLICATIONS

International Preliminary Report on Patentability for corresponding application PCT/EP2015/075671 filed Nov. 4, 2015; dated May 18, 2017.

\* cited by examiner

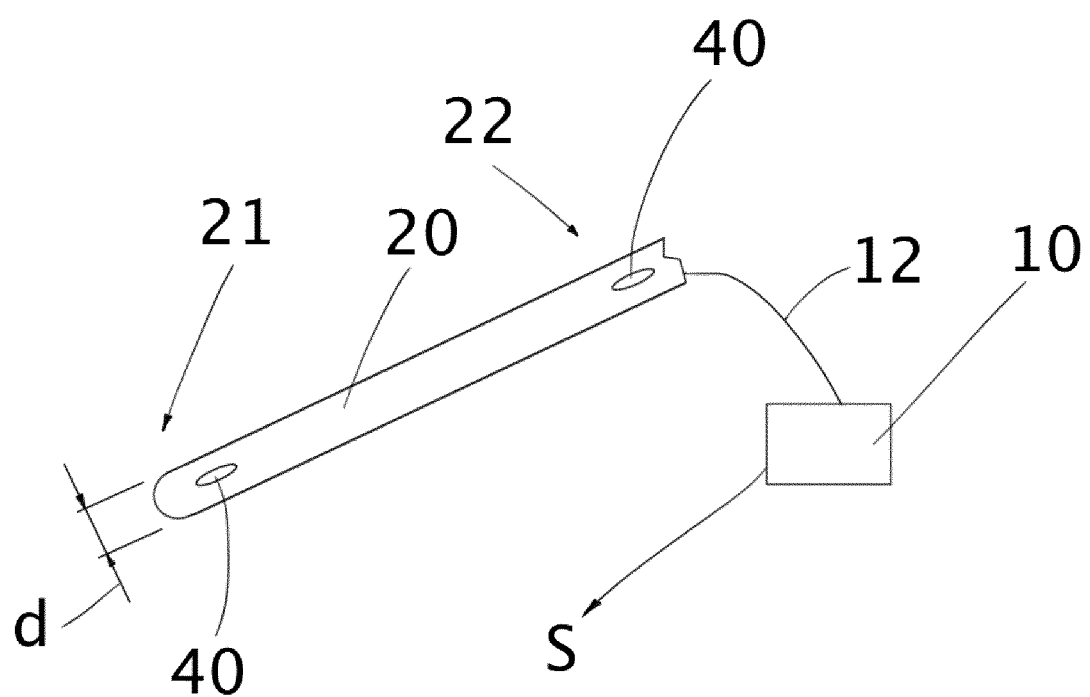

MONITORING SYSTEM

TECHNICAL FIELD

The present invention relates to a monitoring system for endoscopic treatments, in particular for use in endourological interventions, as well as to a method for monitoring ambient conditions, in particular for acquiring pressures in endourological interventions, with at least one measurement device.

BACKGROUND

A rinsing stream is used in endourology to clean the lens of the endoscope along with the treatment zone and enable a good view, and is provided via a working channel of the endoscope or a separate rinsing channel. In further developing the used instruments or endoscopes, the goal is to work with ever smaller diameters to keep traumatization to the tissue as low as possible. As a consequence, the existing working channels of the instruments, e.g., those used for rinsing but also for siphoning, are also getting ever smaller. High rinsing streams, e.g., short, high-pressure ones for flushing the treatment zone, thus quickly trigger a significant pressure increase inside of the body, since the liquid cannot be siphoned away fast enough through the smaller working channels. Since the kidney is a very pressure-sensitive organ, already slight intrarenal pressure increases can lead to glomerular kidney damage, and thus to renal failure. At an excessively high intraoperative pressure, there is also the risk that contaminated liquid from the urinary track will be increasingly absorbed by the body, resulting in postoperative trauma or even sepsis. On the other hand, a certain excess pressure in the hollow organs to be examined is also necessary so as to dilate the latter for better instrumental and optical access, and prevent a collapse during the intervention.

BRIEF SUMMARY

Therefore, the aim of the disclosure is to indicate a monitoring system for endoscopic treatments, in particular for endourological interventions, a method for monitoring ambient conditions, in particular for acquiring pressures in endourological interventions, as well as to provide a guidewire, which make it possible to reliably and easily determine ambient conditions, in particular enabling pressures and/or pressure changes and minimize the risks to the patients.

According to the invention, a monitoring system for endourological treatments comprises an evaluation unit and a guidewire, which comprises at least one measuring device, wherein the evaluation unit can receive data of the at least one measuring device, and wherein the evaluation unit comprises a comparator, which compares the data with a comparison value.

The monitoring system of the kind in question can be used for all types of endoscopic interventions that utilize a rinsing stream. These are in particular the treatment of kidney, ureteral and bladder stones, elimination of renal compression, interventions on the prostate, bladder or urethra, and visual inspections of the urinary tract. The access can be gained via natural body orifices, or also via surgically created openings. Particular emphasis must be placed on use of the invention for lithotripsy, wherein it makes no difference what kind of lithotripters are used. Advantageously the endoscope comprises at least one rinsing channel, which is designed to rinse a lens of the endoscope or treatment zone with a medium, e.g., a sterile liquid, so as to enable or improve the view on the treatment zone, and in particular on the body stones to be crushed. In addition, the endoscope can also exhibit at least one suction channel, e.g., so as to siphon liquid, but also particles (e.g., from the body stones), out of the treatment zone.

Favorably the monitoring system now serves to check or monitor the ambient conditions in the treatment zone, wherein the monitoring system to this end favorably encompasses the guidewire, which can be guided to the treatment zone. Guidewires of the kind in question are known from prior art in terms of their basic structure. Preferably a guidewire is used made of metal or plastic (or a mixture or combination of the two materials), which consists at the distal end of a softer, more flexible material, so as to ensure the best possible flexibility and to minimize the risk of injuries (during introduction into the body). Advantageously at least regions of the guidewire are hydrophilic in design and/or also provided with a PTFE coating (polytetrafluoroethylene) to improve slip properties. The guidewire exhibits a diameter of about 0.15 to 3 mm, preferably of about 0.4 to 2 mm, and very especially preferably of about 0.8 to 1.2 mm. Otherwise, reference can be made to the embodiments known from prior art with respect to the geometric and structural configuration of the guidewire. The same holds true in terms of the at least one measuring device.

Depending on what value or which data are to be acquired, for example a corresponding pressure, temperature or force sensor, etc. is integrated, which can acquire the ambient conditions. The temperature measurement can also be executed with the pressure sensor, it is advantageous for a more precise measurement, however, that the temperature sensor be designed separately, and secured in proximity to but spaced apart from the pressure sensor. It is critical that the monitoring system comprise the evaluation unit, which can acquire data, in particular measuring data, from the at least one measuring device.

The data transmission can thereby take place both wired and wireless, e.g., via a corresponding transmitter. Advantageously the evaluation unit here comprises the comparator, which compares the data received or acquired from the measuring device with a comparison value. Let it be noted at this juncture that, as a rule, direct use is not made of the data received from the measuring device. Sensors usually output a voltage or current signal, which is first converted or transformed into an appropriate corresponding value for a pressure, temperature or force. The comparison value can thus specifically be a temperature, a pressure or a force.

Likewise, however, the comparison value can also be a purely technical value, e.g., a voltage signal or current signal. It is important that the evaluation unit or comparator compare the data with the comparison value, and can thereby recognize, for example, if the data received from the measuring device have exceeded/dropped below the comparison value, possibly corrected by a predetermined correction value, since it can then be determined whether the ambient conditions lie in an unfavorable range, e.g., whether a temperature is too low/high or a pressure is too low/high.

The evaluation unit can be arranged in the guidewire, e.g., in/on a proximal end of the guidewire, but can also be connected with the actual guidewire by a cable and corresponding data line, e.g., also via a plug connection. Advantageously the evaluation unit is best integrated into a suitable control part/handset, which advantageously is situated at the proximal end of the guidewire. With regard to the evaluation unit, let it further be noted that this case preferably does involve a small computing unit, such as a processor. The comparator can be a part or module of this computer, but can also be defined by the functionality of the latter, i.e., not be a unit separate from the latter, but rather only take the form of a program run on the computer.

In a preferred embodiment, the at least one measuring device comprises a pressure or pressure change. Favorably a pressure sensor is, therefore, used, wherein piezoresistive, piezoelectric, capacitive or inductive pressure sensors are here preferably utilized. A corresponding current/voltage supply, which could possibly be required for the measuring device(s), can be provided via the guidewire and as the case may be via or from the evaluation unit. The comparison value is thus advantageously a pressure value. A pressure value or pressure level can thus be prescribed, with which the pressures acquired by the measuring device are compared. The comparison value can here be an absolute pressure, for example which cannot be exceeded/dropped below. The comparison value can also be a relative pressure too, which relates to a starting pressure level. Consequently, it can advantageously be easily determined when a pressure threshold has been exceeded/dropped below based upon a reference value (compared starting pressure level). The reference value here favorably represents the pressure value that would normally prevail in the corresponding body zone/treatment zone or prevails there prior to the treatment. It measures about 10 cm water column (1 kPa) in endourological interventions. During such an intervention, the renal pressure is increased by the suction-rinsing system to values of between about 40 and 50 cm water column (4 to 5 kPa). If the pressure rises to above 150 cm water column (15 kPa), damages to the kidney are likely. Based upon current experience, the comparison value that should best not be exceeded measures about 100 to 120 cm water (10 to 12 kPa), and in one alternative of the invention can be individually tailored to each patient using a correction value. The measuring device should be capable of evaluating pressure values of up to 300 cm water column (30 kPa).

In another preferred embodiment of the present invention, the at least one measuring device acquires a temperature or a temperature change. Use is favorably also made of a temperature sensor, wherein semiconductor-based temperature sensors (so-called chip sensors) are here preferably utilized. The temperature can also be detected with the previously described pressure sensor. The measurements described above, the reference value, the comparison value, the relative value, etc. for the pressure also apply mutatis mutandis to the temperature. A comparison with a reference value is important here as well, i.e., the change in temperature during the intervention, and less so the absolute temperature value.

The temperature sensor is important especially in laser treatments, which as a rule increase the temperature in the treatment zone, e.g., while crushing stones in the kidney or bladder. For example, this can be offset by increasing the rinsing agent throughput, even though this in turn might raise the pressure in the treatment zone. Therefore, it is recommended to measure both, i.e., the pressure and temperature, since the laser power might also have to be lowered or suspended. For example, a temperature increase also arises when the rinsing agent throughput is interrupted (e.g., due to a clogged line). The data and temperature pressure obtained by the evaluation unit (see in detail further below) can then also be used for regulating the rinsing liquid or treatment device, e.g., the laser.

The evaluation unit preferably comprises an input unit, which can be used to set the comparison value or adjust it with a correction value, wherein the evaluation unit preferably also comprises a plurality of comparison values or correction values. One or several comparison values can thus be advantageously prescribed and adjusted by an attending physician, for example. For example, a comparison value can be an absolute value that can never be exceeded, or damaging organs like the ureter system is imminent. Another comparison value or alternative correction value can be a patient-specific value. As a result, individual consideration can be given to a patient. For example, there might be a patient who is extremely sensitive or biased, but the pressure or temperature would still be far removed from critical values in the treatment zone. The monitoring system allows the attending physician to easily and quickly determine these differences and react accordingly. In order to adjust the comparison value and/or to prescribe various comparison values, the evaluation unit or its entry unit best exhibits a touchpad or corresponding control knobs. In particular, a display or the like is also provided so as to view or check the set comparative value(s) or correction value(s).

The evaluation unit preferably comprises an output device, which generates an output signal that indicates when the comparison value has been exceeded/dropped below. The output signal can be a corresponding warning sound or an optical signal, which alerts the attending physician. Also possible is a haptic feedback that involves a vibrating or shaking of the already mentioned handset/control panel. The measurement information can also be transmitted to a central unit, which handles the evaluation and information of the user. Advantageously it can be prescribed whether the output signal should be generated when the comparison value is exceeded or dropped below. Based on the output signal, the attending physician can advantageously react quickly, and if necessary reduce the rinsing stream, increase the suction power, or generally briefly suspended the treatment. Both the input unit and output unit can be designed as modules separate from the evaluation unit, which best can also be arranged in the control panel/handset.

The evaluation unit preferably generates various output signals, depending on which comparison value or correction value was exceeded/dropped below. It can here also be possible to provide various output signals depending on which the comparison value is exceeded/dropped below, e.g., via different pitches or different color signals. If several measuring devices are provided at various positions on the guidewire, the various output signals can also correlate with the different positions of the measuring devices, so as to indicate to the attending physician where problems might be expected. The output signal or its type and configuration can also be dependent on whether a comparison value is exceeded or dropped below.

Advantageously the evaluation unit also acquires how often and/or how long the comparison value is exceeded/dropped below. Preferably the evaluation unit also acquires how long a comparison value is exceeded. As a result, it may not be necessary to generate an output signal right away if a comparison value is exceeded one time. Instead, the evaluation unit best acquires how often, how long and/or by how much a comparison value is or was exceeded, and depending thereon outputs the output signal. It goes without saying that this functionality can correspondingly be parameterized by a user, for example via the input unit. Let it basically be noted at this juncture that the comparison value can just as well be a comparison range. Therefore, it can definitely be advantageous not to prescribe a specific value, but rather a range with an upper and lower limit. This is especially helpful in reacting to pressure fluctuations that can be traced back to the measuring device(s) or the measuring accuracy thereof.

Advantageously the evaluation unit generates a control signal for another device, in particular for a suction-rinsing system, when the comparison value is or has been exceeded/dropped below. For example, the comparison value exceeding the control signal has a direct influence on the rinsing stream of the endoscope. In other words, the monitoring means can directly influence another device, e.g., here the suction-rinsing system and its rinsing function, if the monitoring system recognizes that comparison values, meaning in other words permissible threshold values, are being exceeded. With respect to the pressure and/or temperature in the treatment zone, the latter could thus be quickly reduced by decreasing the rinsing stream or increasing the suction power. It is understood that control signal transmission can be both wired or wireless.

In a preferred embodiment, the at least one measuring device is calibrated by the evaluation unit, in particular by setting an acquired or received pressure level to zero. This enables an extremely simple and safe system. The principle was already explained in conjunction with the relative pressure comparison value. The measuring device is advantageously calibrated before the surgical intervention or examination starts, once the endoscope has already been guided to the treatment zone (intracorporally). For this purpose, the aforementioned control panel/handset favorably exhibits a corresponding lever, button or switch. However, this function is best also integrated into any touchpad that might be present. The pressure or temperature or force acquired at this instant is now set to zero or taken as the reference value, and it is easy to prescribe a comparison value potentially adjusted by a correction value and corresponding to the distance from this reference value. The "normal" pressure/temperature/force in the treatment zone is thus acquired first. The monitoring system favorably recognizes a deviation from this "normal" pressure/temperature/force, and reports the latter via the output signal(s). This configuration is extremely simple and safe, and does not require the use of what are usually expensive and complicated absolute pressure sensors or corresponding sensors for temperature or force.

The at least one measuring device, e.g., the pressure sensor, is preferably arranged at a distance of about 2 to 5 cm from the distal end of the guidewire. The last 2 to 3 cm of a guidewire usually have a highly flexible design, so as to achieve better controllability and less traumatization to the surrounding tissue. The pressure sensor is thus preferably located near the distal end of the guidewire, but not inside of the highly flexible region, so as not to impair its function. If the highly flexible region extends over a greater length, the pressure sensor is located correspondingly further away from the distal end of the guidewire. In the absence of a highly flexible region, a maximum distance of the at least one measuring device, in particular of a pressure sensor, from a distal end of the guidewire measures less than about 20 mm, preferably less than about 10 mm. This provides the best possible option for acquiring the ambient conditions, and thus in particular the pressures and pressure changes in the areas in front of the sensor. However, it is also conceivable that the sensor be situated inside or at the proximal end of the guidewire, and connected with communicating pipes inside of the guidewire to one or more openings in the distal region of the guidewire. Depending on the corresponding measurement technology, the at least one measuring device can be arranged on a surface as well as inside of the guidewire. If the measuring device is situated on a surface of the guidewire, dynamic effects and the back pressure can advantageously also be acquired. It is understood that a plurality of measuring devices can also be provided, which can be arranged both inside and outside of the guidewire. These measuring devices need also not all be of the same type. When using several measuring devices, profiles such as pressure profiles, temperature profiles or force profiles can also be generated along the guidewire. For example, this could make it possible to infer to what extent pressure can be reduced in the treatment zone. Any problems that might arise around the treatment zone can also be indicated. Let it basically be noted that it can be extremely advantageous to provide at least one location or position sensor on the guidewire, so that the position and location of the guidewire relative to the body can be determined, and thus potentially the site of an elevated pressure.

In an alternative embodiment, at least one measuring device is a relative pressure sensor, and at least one additional measuring device is an absolute pressure sensor, wherein the relative pressure sensor is preferably arranged at a distal end of the guidewire, while the absolute pressure sensor is preferably arranged at a proximal end of the guidewire. Advantageously the absolute pressure sensor can be used to calibrate the relative pressure sensor.

Apart from the pressure sensor, the additional measuring device can be a temperature sensor, wherein the temperature sensor is also preferably arranged at a distal end of the guidewire, i.e., in the treatment zone, in proximity to, yet spaced apart from the pressure sensor. For example, the distance measures 2-10 mm, preferably 3-6 mm.

According to the invention, a method for monitoring ambient conditions, in particular for acquiring pressures in endoscopic treatments or endourological interventions, with a monitoring system that exhibits an evaluation unit and guidewire with at least one measuring device, comprises the following steps:

Receiving data of the at least one measuring device via the evaluation unit;

Comparing the data with a comparison value.

The method preferably further comprises the following steps:

Zeroing out a pressure and/or temperature and/or force level acquired by means of the at least one measuring device;

Starting a treatment, in particular an endoscopic treatment or an endourological intervention.

It goes without saying that the advantages and features of the monitoring system apply analogously and correspondingly to the method, and vice versa.

According to the invention, a guidewire is provided with at least one measuring device, which exhibits the aforementioned advantages and features of the monitoring system and the method.

BRIEF DESCRIPTION OF THE DRAWING

Additional advantages and features arise from the following description of a preferred embodiment of the monitoring system according to the invention, the method according to the invention, as well as the guidewire according to the invention, drawing reference to the attached FIGURE.

Shown on:

FIG. 1: is a schematic view of a preferred embodiment of the monitoring system.

DETAILED DESCRIPTION

FIG. 1 presents a schematic view of a guidewire 20, which exhibits a measuring device 40 at a distal end 21. A measuring device 40 is also provided at a proximal end 22 of the guidewire 20. The guidewire 20 is electrically connected with an evaluation unit 10 by a cable 12. As an alternative, the connection can preferably also be wireless. The evaluation unit 10 basically must not also be arranged separately from the guidewire 20, but can rather comprise part of the latter. Advantageously one end of the guidewire 20 is also provided with a control panel/handset, which comprise the evaluation unit 10. An input unit and output unit can also be provided in the control panel/handset, so as to both enable user inputs and relay output signals. Not shown is a current or voltage supply, which might also have to be provided for the measuring devices 40. A diameter d of the guidewire ranges from 0.15 mm to 3 mm, favorably in a range of 0.4 to 2 mm, and very especially preferably ranges from about 0.8 to 1.2 mm. The diameter d can vary over the length of the guidewire, but rather tends to be constant in preferred embodiments. Reference sign S schematically denotes that control signals are here output proceeding from the evaluation unit 10, so as to regulate or control another device, for example a suction-rinsing system.

The invention claimed is:

1. Monitoring system for endoscopic treatments comprising
    an evaluation unit and a guidewire, which comprises at least one measuring device, wherein the guidewire has a diameter between 1 mm and 1.5-mm,
    wherein the evaluation unit receive data from the at least one measuring device, so as to monitor ambient conditions in a treatment zone, and
    wherein the evaluation unit comprises a comparator, which compares the data with a comparison value to determine that the ambient conditions lie within an unfavorable range;
    wherein the system is configured such that the comparison value is referred to a reference value acquired through the at least one measuring device in the treatment zone before a surgical intervention or an examination starts by an endoscope having been guided in the treatment zone;
    wherein the evaluation unit comprises an input unit which is used to adjust the comparison value and wherein the evaluation unit comprises a plurality of comparison values;
    wherein the evaluation unit is configured to generate a control signal for another device when the comparison value is exceeded;
    wherein the another device is a suction rinsing system; and
    wherein the comparison value is an absolute value and another comparison value is a patient specific value, wherein the least one measuring device is a relative pressure sensor, and at least one additional measuring device is an absolute pressure sensor, and wherein the relative pressure sensor is arranged at a distal end of the guidewire, while the absolute pressure sensor is arranged at a proximal end of the guidewire.

2. Monitoring system according to claim 1, wherein the at least one measuring device acquires a pressure or pressure change and/or a temperature or temperature change.

3. Monitoring system according to claim 1, wherein the evaluation unit comprises an output unit, which generates an output signal that indicates when the comparison value has been exceeded.

4. Monitoring system according to claim 1, wherein the at least one measuring device can be calibrated by the evaluation unit.

5. Monitoring system according to claim 1, wherein the at least one measuring device is arranged at the distal end of the guidewire.

6. Guidewire with the at least one measuring device according to claim 1.

7. Monitoring system according to claim 1, wherein the evaluation unit comprises a plurality of comparison values.

8. Monitoring system according to claim 4, wherein the calibration of the at least one measuring device comprising setting a pressure and/or temperature level to zero.

9. Monitoring system according to claim 1, the guidewire has a diameter between 1 and 1.2 mm.

* * * * *